United States Patent [19]
Rosenberg et al.

[11] Patent Number: 5,961,535
[45] Date of Patent: Oct. 5, 1999

[54] INSTRUMENT AND METHOD FOR SURGICAL STIMULATION OF CONNECTIVE TISSUE

[76] Inventors: Thomas D. Rosenberg, 2540 Haven La., Salt Lake City, Utah 84117; Richard M. Greenwald, 4972 Ponderosa Ct., Park City, Utah 84098

[ * ] Notice: This patent issued on a continued prosecution application filed under 37 CFR 1.53(d), and is subject to the twenty year patent term provisions of 35 U.S.C. 154(a)(2).

[21] Appl. No.: 08/734,465

[22] Filed: Oct. 17, 1996

[51] Int. Cl.⁶ .................................................. A61B 17/00
[52] U.S. Cl. ............................................. 606/184; 606/1
[58] Field of Search ............................. 606/1, 185, 186, 606/201, 204; 601/135, 137

[56] References Cited

U.S. PATENT DOCUMENTS

| | | | |
|---|---|---|---|
| 4,705 | 8/1846 | Tieman | 606/186 |
| 8,386 | 8/1851 | Tieman | 606/183 |
| 693,554 | 2/1902 | Langstaff | 606/186 |
| 3,221,739 | 12/1965 | Rosenthal . | |
| 3,994,301 | 11/1976 | Agris . | |
| 4,417,580 | 11/1983 | Birchmeier . | |
| 4,985,035 | 1/1991 | Torre . | |
| 5,217,463 | 6/1993 | Mikhail . | |
| 5,250,067 | 10/1993 | Gelfer . | |
| 5,269,800 | 12/1993 | Davis . | |
| 5,352,219 | 10/1994 | Reddy . | |
| 5,387,223 | 2/1995 | Agee . | |
| 5,458,611 | 10/1995 | Resnick . | |

FOREIGN PATENT DOCUMENTS

| | | | |
|---|---|---|---|
| 674 415 | 6/1966 | Belgium . | |
| 22 59 229 | 6/1974 | Germany . | |
| 0209631 | 1/1968 | U.S.S.R. . | |
| 0000173 | of 1869 | United Kingdom | 606/183 |
| 998185 | of 1965 | United Kingdom . | |
| WO 93/05720 | 4/1993 | WIPO . | |
| WO 93/15665 | 8/1993 | WIPO . | |

*Primary Examiner*—Michael Buiz
*Assistant Examiner*—William Lewis
*Attorney, Agent, or Firm*—Clayton Howarth & Cannon, P.C.

[57] ABSTRACT

An instrument and method for surgical stimulation of connective tissue are disclosed. The instrument has a plurality of protuberances located on a head connected to a shaft and a handle for manipulation by a surgeon to selectively perforate diseased connective tissue to stimulate a variety of desirable biological responses resulting from bleeding from the intrinsic vasculature of the connective tissue, investing tissue, and adjoining bone.

16 Claims, 1 Drawing Sheet

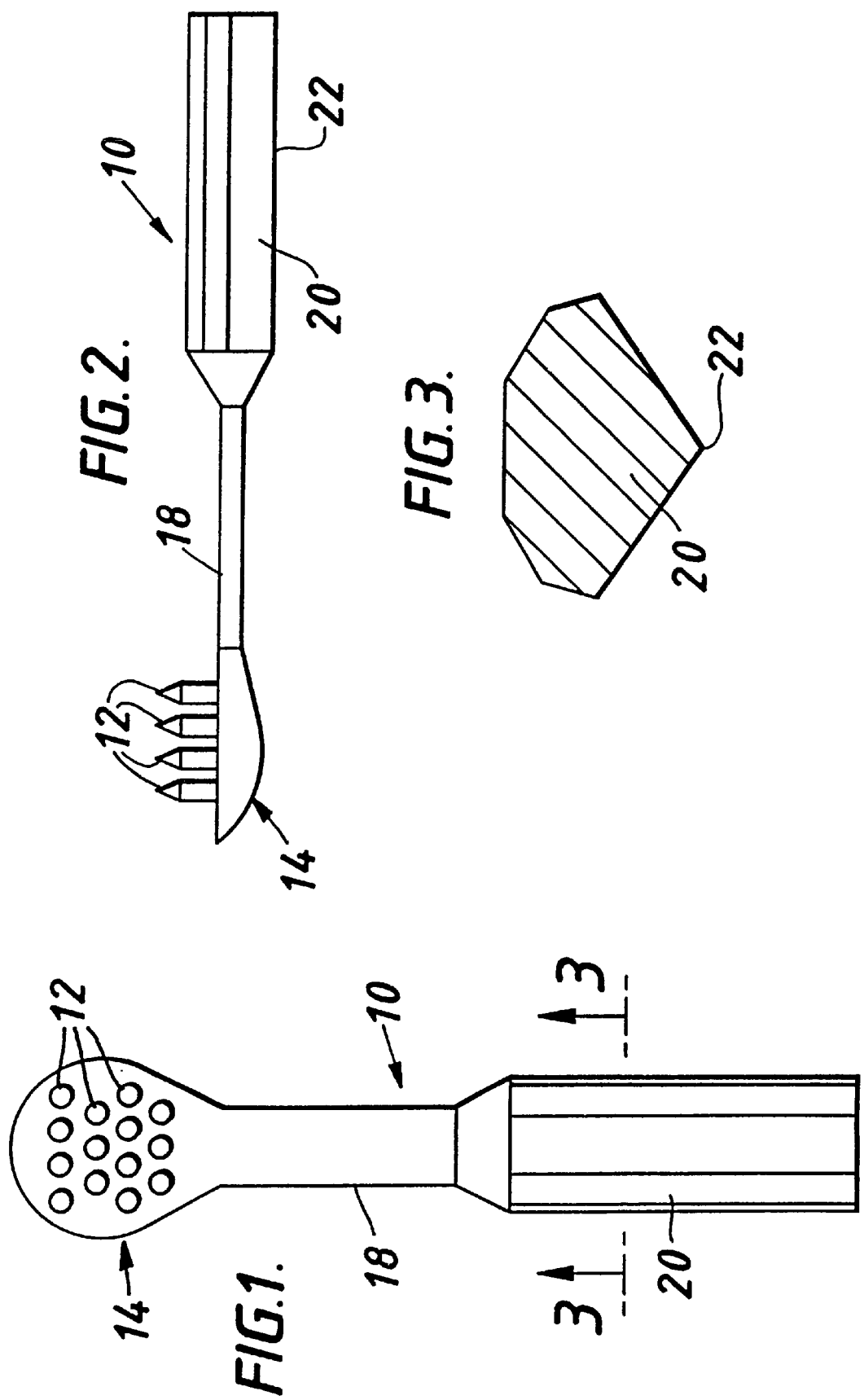

INSTRUMENT AND METHOD FOR SURGICAL STIMULATION OF CONNECTIVE TISSUE

BACKGROUND

1. The Field of the Invention.

The present invention relates generally to an apparatus and method to treat abnormal connective tissues of mammals, and is particularly directed to an instrument and method of treatment by which said connective tissue can be perforated to produce a desirable response such as inflammation, cell proliferation, collagen synthesis, or fibrous healing.

2. Description of The Related Art and Background of the Invention.

There are a number of conditions and diseases which can produce a negative effect in connective tissue such as, for example, mechanical trauma to a tendinous or ligamentous tissues leading to laxity of the traumatized tissue. One common condition occurs when the medial collateral ligament of the knee is injured in connection with the anterior cruciate ligament. While the medial collateral ligament typically will heal on its own acutely, the additional instability afforded by the condition of the anterior cruciate ligament rupture may compromise the medial collateral ligament healing.

The chronically lax medial collateral ligament in this combined medial collateral ligament/anterior cruciate ligament injury, has either been untreated or treated with drastic surgical procedures. In the example provided, the anterior cruciate ligament has been surgically reconstructed and the medial complex has been surgically mobilized and advanced either partially or completely, resulting in increased tissue tension. The medial collateral ligament tissue is then fixed with sutures, staples, ligament washers, or soft tissue fixation. These "take down-put back" procedures may be unnecessary and can interfere with an optimal healing process. They may disrupt the Sharpey's fibers at one end, may impair the nervous and vascular function of the tissue and may produce a pressure necrosis either at a refixation point or by suture strangulation. These procedures are only exemplary of many conditions and procedures involving connective tissue to which the common treatment is invasive, requiring of implants or sutures, and mechanical.

Accordingly, there is a need in the art for a method of treating connective tissue abnormalities which does not require surgical reconstruction, but rather which relies on a biologic response to mechanical stimulation of connective tissue.

OBJECT AND SUMMARY OF THE INVENTION

It is, therefore, an object of the present invention to provide an instrument and method for surgical mechanical stimulation of abnormal connective tissue to produce a desired biological response conducive to healing of the abnormal tissue. The above object, as well as others, are realized in a specific illustrative embodiment of an instrument which has sharp pointed protuberances to puncture connective tissues and investing tissues including intrinsic vasculature and possibly adjoining bone to stimulate a biological response such as inflammation, cell proliferation, collagen synthesis, or fibrous healing. It will be understood that these responses may serve as alternatives to more invasive mechanical and surgical procedures commonly used.

BRIEF DESCRIPTION OF THE DRAWINGS

The above and other objects, features and advantages of the invention will become apparent from a consideration of the subsequent detailed description presented in connection with the accompanying drawings in which:

FIG. 1 is a top plane view of an instrument for stimulation of connective tissue in accordance with the present invention;

FIG. 2 is a side view of the instrument of FIG. 1; and

FIG. 3 is an end cross sectional view of the instrument of FIG. 1 taken along the line 3–3.

DETAILED DESCRIPTION OF THE PREFERRED EMBODIMENT OF THE PRESENT INVENTION

Reference will now be made to the drawings wherein like structures will be provided with like reference numerals.

Referring to FIGS. 1-2, there is shown, generally designated at 10, an instrument for surgical stimulation of connective tissue. The instrument includes a plurality of sharp protuberances 12, extending generally in parallel outwardly from a shaft 18. The protuberances can be fashioned from any potentially sterilizable rigid material that will maintain a sharp point. For example surgical grade stainless steel and titanium metals, as well as ceramic, would be suitable materials. These materials are generally known for use in multiple use instruments which can be repeatedly sterilized. The protuberances 12 could also be made of less expensive polymers if the device is intended for single use.

A head 14 may be formed integrally with the shaft 18 and a handle 20 or a head 14 may be formed separately therefrom. It will be appreciated that these can be formed of similar materials to the protuberances. It is presently preferred to use surgical grade stainless steel. The shaft 18 is depicted as linear in the preferred embodiment, but it will be appreciated that a variety of shapes could be used to address a variety of different surgical procedures, surgeon preferences, and patient geometries.

Size could also vary. It will be appreciated that a smaller instrument will be called for in delicate procedures of the hand, as opposed to more rigorous applications such as knee procedures. It will also be appreciated that some arthroscopic applications may require that a miniaturized version be used with well known cooperative instrumentation.

The handle 20, of course, serves as the focus of control for the surgeon. The shaft 18 conveys the manipulation exerted on the handle 20 to the protuberance 12.

The protuberances 12 can be fitted to the shaft 18 or a head 14 by commonly known procedures such as frictional exertion of tight fitting protuberances into holes in the head. Adhesives or welding may also be used. In the presently preferred embodiment, the protuberances 12 are arrayed in parallel, all orthogonal to the plane of the head. It will be appreciated that protuberances 12 could be affixed to a cylindrical head in a radial fashion, or other configurations.

The presently preferred number of protuberances is approximately fourteen. The number and size of protuberances will vary with application. For example, in surgical procedures in which the surface area of the operative connective tissue is small, a smaller number of protuberances will be required. Typically, a large number of perforations are required to achieve the desired response. It will be appreciated that the procedure is accomplished more effectively and in a more uniform manner if the perforations can be made with minimized manipulation of the inventive instrument afforded by the optimal number of protuberances.

It will also be appreciated that a variety of different head and shaft configurations could be detachably affixed to the handle.

Now, referring to FIG. 3, wherein an end cross-section of the handle 20 of FIGS. 1 and 2 is depicted. The handle 20 has a lower protuberance or needle 22 extending in the opposite direction from protuberances 12. This provides a tactile means for a surgeon to detect the orientation of the protuberances 12 upon insertion of the instrument into a body cavity out of direct view to the surgeon. It will also be appreciated that visual or other means could be provided for this purpose.

The instrument is used by applying the pointed ends of the protuberances to abnormal, diseased or damaged connective tissue. This results in perforation of the connective tissue, investing tissues, and their intrinsic vasculature, as well as possibly adjoining bone. Resultant bleeding contributes to a desired biological response including inflammation, cell proliferation, collagen synthesis, or fibrous healing.

The biological response could be viewed as a process that begins with the bleeding. The bleeding begins a process in which multiple areas of tissue are stimulated. For each area of tissue to be stimulated the process is used one time only.

The biological response process has been shown to reduce medial laxity by one grade in subjective testing. The instrument also provides means for limiting pathological laxity.

The method described can be applied in any procedural context wherein the surgeon has access to target connective tissue. For example, it is well adapted to subcutaneous and submuscular surgical procedures in the embodiment described. A typical surgical procedure presently used in the art involves arthrotomy. The instrument of the present invention is well adapted to that procedure. The inventive method described herein is also well adapted to arthroscopic procedures in conjunction with other devices and procedures known and practiced in the art. An elongate flexible shaft (not depicted) and relatively small head 14 is called for in arthroscopic applications.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. An instrument for stimulation of connective tissue comprising:

a handle for gripping by a user;

an elongate shaft fixedly connected to and extending outwardly from the handle; and a plurality of protuberance means fixedly connected to and extending outwardly from the shaft for substantially simultaneous perforation of abnormal connective tissue when so manipulated by a user gripping and manipulating the handle;

wherein the plurality of protuberances are disposed in a substlmtially orthgonal direction with regard to the shaft.

2. An instrument for stimulation of connective tissue as in claim 1 wherein the handle further comprises locator means for determining the orientation of the protuberance means.

3. An instrument for stimulation of connective tissue as in claim 2 wherein the locator means are visually perceptible.

4. An instrument for stimulation of connective tissue as in claim 2 wherein the locator means are tactilely perceptible.

5. An instrument for stimulation of connective tissue as in claim 1 wherein the protuberance means are metal.

6. An instrument for stimulation of connective tissue as in claim 1 wherein the protuberance means are polymeric.

7. An instrument for stimulation of connective tissue as in claim 1 wherein the plurality of protuberances are disposed in a substantially parallel orientation with each other.

8. A method for stimulation of connective tissue comprising the steps of:

providing an instrument with a plurality of protuberances and a handle;

manipulation of the protuberances by means of the handle in a surgical procedure to perforate abnormal connective tissue to stimulate bleeding and a resultant biological response in the connective tissue.

9. A method for stimulation as in claim 8 wherein the surgical procedure is subcutaneous.

10. A method for stimulation as in claim 8 wherein the surgical procedure is arthroscopic.

11. A method for stimulation as in claim 8 wherein the surgical procedure is submuscular.

12. A method for stimulation as in claim 8 wherein the surgical procedure is by arthromy.

13. A method as in claim 8 wherein the biological response is inflammation.

14. A method as in claim 8 wherein the biological response is cell proliferation.

15. A method as in claim 8 wherein the biological response is collagen synthesis.

16. A method as in claim 8 wherein the biological response is fibrous healing.

* * * * *